United States Patent [19]

Graziani et al.

[11] Patent Number: 4,542,252
[45] Date of Patent: Sep. 17, 1985

[54] MULTI-STAGE ADIABATIC PROCESS FOR METHANOL CONVERSION TO LIGHT OLEFINS

[75] Inventors: Kenneth R. Graziani, Thorofare; Ajit V. Sapre, West Deptford, both of N.J.

[73] Assignee: Mobil Oil Corporation, New York, N.Y.

[21] Appl. No.: 632,739

[22] Filed: Jul. 20, 1984

[51] Int. Cl.$^4$ ............................................. C07C 1/20
[52] U.S. Cl. ................................. 585/640; 585/408; 585/324; 585/315; 585/469; 585/733; 422/200
[58] Field of Search ............... 422/200, 194; 585/408, 585/324, 315, 469, 640, 733

[56] References Cited

U.S. PATENT DOCUMENTS

| | | | |
|---|---|---|---|
| 2,299,197 | 10/1942 | West | 422/200 |
| 2,596,299 | 5/1952 | Simpson | 422/200 |
| 3,433,600 | 3/1969 | Christensen | 422/194 |
| 3,931,349 | 1/1976 | Kuo | 585/469 |
| 4,025,571 | 5/1977 | Lago | 585/469 |
| 4,058,576 | 11/1977 | Chang et al. | 585/640 |
| 4,100,219 | 7/1978 | Rodewald | 585/469 |
| 4,404,414 | 9/1983 | Penick et al. | 585/469 |

OTHER PUBLICATIONS

Perry, "Chemical Engineer's Handbook", 5th Ed. McGraw-Hill (1973), pp. 4-20 to 4-21.

Primary Examiner—D. E. Gantz
Assistant Examiner—A. Pal
Attorney, Agent, or Firm—A. J. McKillop; M. G. Gilman; J. F. Powers, Jr.

[57] ABSTRACT

The operating performance of a multi-stage fixed bed adiabatic reactor system with interstage cooling designed for the exothermic conversion of methanol to light olefins is improved by cofeeding small quantities of light olefins with the methanol feed whereby a more controllable operation is achieved. Catalyst activity and cycle length also improves significantly. The light olefins can be produced in situ during dehydration.

19 Claims, 6 Drawing Figures

Fig. 4
EFFECT OF PROPYLENE COFEED

Fig. 5
COMPARISON OF TEMPERATURE PROFILES

Fig. 6

MULTI-STAGE ADIABATIC PROCESS FOR METHANOL CONVERSION TO LIGHT OLEFINS

BACKGROUND OF THE INVENTION

1. Field of the Invention

This invention relates to the production of olefins from a lower aliphatic alcohol, its corresponding ether or mixtures thereof. More particularly, it relates to the catalytic conversion of a methanol feed to an olefinic product. This invention especially relates to improvements in the conversion of a methanol feed to an olefinic product in a fixed bed adiabatic reactor system.

2. Description of the Prior Art

The petrochemical industry has undergone tremendous growth in the past few decades. The production of synthetic fibers, plastics and petrochemicals by this and allied industries has steadily grown, at least in part, because of the availability of increasing supplies of inexpensive petrochemical raw materials, such as ethylene, propylene and other olefins. The principal source of ethylene at the present time is from steam cracked petroleum naphtha. The manufacture of polyethylene and styrene monomer utilizes a significant portion of this ethylene feed.

The ever-increasing demand for olefinic feedstocks has periodically caused a shortage of these basic raw materials either because of a limitation in petroleum feedstocks of suitable quality or a limitation in naphtha cracking capacity. An alternate source of ethylene from non-petroleum sources is one obvious means of keeping pace with the demand for ethylene and other olefins.

In recent years the patent art has disclosed that methanol and/or dimethyl ether, which may be obtained from coal, natural gas or biomass, can be converted to more complex hydrocarbons, such as olefins and aromatics, by utilizing a novel group of zeolites, exemplified by ZSM-5 zeolites. Ethylene is one of the olefinic hydrocarbons which may be obtained in this catalytic conversion. The reaction is highly exothermic and the olefins initially formed have a tendency to undergo further reaction to produce aromatic hydrocarbons useful in the production of motor gasoline. A large body of this patent art is concerned with various aspects of the conversion of methanol and/or dimethyl ether to light olefins, particularly ethylene.

The production of olefins from aliphatic ethers by catalytic conversion with a HZSM-5 zeolite catalyst is disclosed in U.S. Pat. No. 3,894,106 of Chang et al.

U.S. Pat. No. 3,979,472 of Butter discloses the conversion of lower alcohols and their ethers with a composite of antimony oxide and a ZSM-5 zeolite to produce a mixture of ethylene, propylene and mononuclear aromatics. U.S. Pat. No. 4,025,572 of Lago discloses that ethylene selectivity can be improved by diluting ZSM-5 with an inert diluent while a similar result is achieved, according to U.S. Pat. No. 4,025,575 of Chang et al, through use of subatmospheric partial pressure of the feed. Selectivity of ethylene is also improved by employing ZSM-5 zeolite in large crystal form of at least about 1 micron either alone (U.S. Pat. No. 4,025,571 of Lago) or in combination with added metals (U.S. Pat. No. 4,148,835 of Chen et al). Better selectivity is also obtained by interdispersing amorphous silica within the interior of the crystalline structure of the zeolite catalyst (U.S. Pat. Nos. 4,060,568 and 4,100,219 of Rodewald).

Although the above-described conversions perform exceptionally well and are unusually effective at converting lower aliphatic alcohols to olefinic hydrocarbons, it has been found that these conversions are exothermic to varying degrees depending on the particular reactant. For example, the amount of heat generated in the conversion of the lower alcohols to hydrocarbon product may be estimated to be in the ranges shown.

| Alcohol Reactant | Heat Produced, BTU per lb of Hydrocarbon Product |
|---|---|
| Methanol | 1000–2000 |
| Ethanol | 200–620 |
| Propanol | 15–360 |

While it is desirable that a reaction be exothermic, since this obviates the need for an external source of heat to drive the reaction, large heat generation loads can require substantial investment in complex reactors with extensive internal cooling means. It can be seen from the above table that the conversion of methanol, and to a lesser degree of ethanol, could be considered excessively exothermic in this regard. Furthermore, because of the inherent character and efficiency of the above-described crystalline aluminosilicate zeolite catalysts, the reaction of methanol, and to a lesser degree of ethanol, tend to be self-accelerating, thereby creating excessively hot local regions, where the reaction tends to go to completion, in the catalyst bed. In an adiabatic catalyst bed reactor, these highly exothermic reactions can result in high catalyst aging rates, and possibly cause thermal damage to the catalyst. Furthermore, such high temperatures could cause an undesirable product distribution to be obtained. Therefore, it is critical in the conversion of methanol to useful products to provide sufficient heat dissipating facilities so that temperatures encountered in any portion of the catalyst sequence are restricted within predetermined limits.

Additionally, it is generally good engineering practice to conduct reactant conversions at elevated pressures to more effectively utilize the reactor volume and attendant equipment. With a methanol charge, however, elevated pressures tend to produce increased quantities of 1,2,4,5-tetramethylbenzene (durene), an undesirable by-product, while lower pressures, e.g. less than 50 psig favor the production of light olefins.

Various techniques have been employed in controlling the exothermic heat released in the catalytic conversion of methanol: U.S. Pat. Nos. 3,931,349 of Kuo (use of light hydrocarbon diluents as heat sink for conversion of methanol to gasoline boiling products), 4,052,479 of Chang et al (operating conditions selected to restrict feed conversion to 5–25%) and 4,238,631 of Daviduk et al (riser reactor and dense fluid catalyst bed). U.S. Pat. No. 4,035,430 of Dwyer et al describes arranging the catalyst in a series of beds of increasing size with interstage quenching with methanol, dimethyl ether and/or light hydrocarbons for controlling exothermic heat. A tubular reactor is disclosed in U.S. Pat. No. 4,058,576 of Chang et al as a means of removing exothermic heat during the catalytic conversion of a lower alcohol to olefins. A two-stage conversion is employed with an alcohol dehydration catalyst utilized in the first stage and a ZSM-5 zeolite in the second stage which is a tubular reactor. In one embodiment, the ZSM-5 catalyst is located in the tubes of the reactor with a heat transfer medium passed through the shell side of the reactor. As the reaction mixture passes through the catalyst, the exothermic heat of reaction is released within the tubes.

U.S. Pat. No. 4,035,430 of Dwyer et al describes a means for controlling the exothermic heat release when converting methanol to gasoline boiling products. After the feed is converted to an equilibrium mixture in a bed of dehydration catalyst, it is passed through a series of zeolite catalyst beds of increasing size with interstage quenching with methanol, dimethyl ether and/or light hydrocarbons to remove the heat of reaction. The exothermic temperature rise in any one of the beds does not exceed about 50° F. and the overall temperature rise does not exceed about 200° F. No details are provided regarding if or how the relative size of the several catalyst beds influences the thermal stability of the desired reaction. Further, there is no suggestion that the procedures may be successfully employed where the alcohol feed is to be converted to predominantly olefinic hydrocarbons vis-a-vis aromatic compounds.

In U.S. Ser. No. 345,985 filed Feb. 5, 1982, it has been found that the exothermic heat generated in the conversion of methanol, its corresponding ether, DME, or mixtures of said alcohol and said ether in the presence of a zeolite catalyst can be effectively removed to provide a stable operation by providing the zeolite catalyst in a series of fixed beds with interstage cooling of the effluent from each bed and by limiting the temperature rise across each bed. In particular, the invention as disclosed therein relates to a process of converting methanol into olefinic hydrocarbon products which comprises:

(a) contacting a feed comprising methanol and water with a dehydration catalyst at elevated temperatures and exothermic reaction conditions effective to convert said alcohol to an ether-rich product, (b) contacting the ether-rich product of step (a) with at least a minimum number of fixed beds of crystalline aluminosilicate zeolite in a sequential manner at elevated temperatures, at substantially the same temperature increase across each of said fixed beds and under exothermic reaction conditions effective to convert said ether-rich product, at a predetermined conversion, to olefinic hydrocarbon products, said temperature increase across each of said fixed beds being no greater than the sensitivity parameter for the conversion of methanol to ethylene, said minimum number of said fixed beds being equal to the ratio of the total adiabatic temperature rise at said predetermined conversion for said methanol-water feed composition to said sensitivity parameter for the conversion of methanol to ethylene, said ratio being a whole number or the next highest whole number when said ratio is not a whole number, and said zeolite being a zeolite having a pore size greater than about 5 Angstrom units, a silica to alumina ratio of at least about 12 and a constraint index of about 1 to 12 or a zeolite characterized by pores, the major dimension of which is less than 6 Angstroms, further characterized by pore windows of about a size such as would be provided by 8-membered rings of oxygen atoms, and (c) cooling the reaction mixture effluent from each of said fixed beds, except the last, to reduce the temperature of said effluent by an amount substantially equal to the temperature increase across said fixed bed.

The entire contents of U.S. Ser. No. 345,985 are incorporated herein by reference.

The primary concern in an adiabatic multi-stage reactor design is the controllability of the operation. This type of reactor can be sensitive to even small changes in operating conditions, and if proper precautions are not taken, operation may become unstable.

It is an object of this invention to convert methanol, dimethyl ether (DME) or mixtures of methanol and dimethyl ether to an olefinic product in a thermally stable process.

It is an another object of this invention to provide a method of improving the stability of a multi-stage fixed bed adiabatic reactor system designed for the exothermic conversion of methanol and/or dimethyl ether to olefinic hydrocarbons in the presence of a zeolite catalyst.

The achievement of these and other objects will be apparent in the following description of the subject invention.

SUMMARY OF THE INVENTION

In accordance with the present invention, it has been found that in the conversion of methanol, its corresponding ether, DME, or mixtures of said alcohol and said ether to an olefinic hydrocarbon product in the presence of a zeolite catalyst in which the zeolite catalyst is provided in an adiabatic multi-stage fixed bed reactor as set forth in U.S. Ser. No. 345,985, the stability of the first-stage of such reactor is most important. Thus, increasing the temperature rise in the first-stage results in an increased temperature rise in the subsequent stages, such that controllability of the first-stage is imperative for the overall stability of the process. It has now been found that the operating performance of a multi-stage fixed bed adiabatic reactor system with interstage cooling designed for the exothermic conversion of methanol and/or dimethyl ether to a hydrocarbon olefinic product can be improved by cofeeding small quantities of light olefins with the methanol and/or dimethyl ether feed. The cofeeding of light olefins to improve reactor stability as in the present invention is unlike the light gas recycle system used in the prior art discussed above in which the primary object is merely to provide a heat sink to control adiabatic temperature rise. In such a system, any inert light gas recycle could be used. The amount of cofed olefins in the present invention, typically about 1 percent by weight of feed is several orders of magnitude lower than the light gas recycle used in the conversion of methanol to gasoline boiling range hydrocarbons. The addition of olefins changes the reaction chemistry, such that the changes in the rate of reaction and hence the heat release is much smaller. Thus the net effect is gain in controllability of the process.

DESCRIPTION OF THE PREFERRED EMBODIMENTS

The present invention relates to improvements in the catalytic conversion of methanol, its corresponding ether, i.e., DME, or mixtures thereof to olefinic hydrocarbons, in a fixed bed reactor system designed to achieve effective control of the exothermic heat release of the reaction. In a preferred embodiment, the reactants comprise methanol and dimethyl ether.

In a preliminary stage of the adiabatic multi-stage reactor system useful in the present invention the methanol reactant is contacted with a dehydration catalyst to produce water and an ether-rich intermediate product. The dehydration catalyst may be any catalyst which results in the intermolecular dehydration of the alcohol reactant to form an ether-rich product of higher carbon to oxygen ratio than the feed.

The dehydration reactions contemplated include those that form simple and mixed ethers such as: dimethyl ether, diethyl ether, and the like. These intermediates may be formed by the intermolecular dehydration of corresponding alcohol reactants, and all of these condensations are exothermic and generate heat. While this dehydration reaction by itself, is generally known with alumina compositions, such as gamma alumina, it is noted that other acidic catalysts known in the art are very effective for the conversion.

Those skilled in the art will recognize that with methanol feed, no intramolecular dehydration is possible, and that therefore the dehydration reaction can only proceed exothermally to form dimethyl ether.

In one embodiment, the operation of a multi-stage reactor system comprises two sequential stages of catalytic contact in which combination both stages are heat generating operations. In the first stage operation the catalytically exothermic heat generation is limited by restricting the conversion of methanol to approximately an equilibrium mixture comprising dimethyl ether, methanol and water. The conversion product or first stage reaction effluent mixture, because of the catalytically generated exothermic heat, has a temperature of about 600° F. to about 750° F. The first stage reaction effluent mixture thus formed is adjusted to a temperature within the range of about 520° F. to about 800° F., depending on the nature of the zeolite catalyst, by passing it through an indirect heat exchange zone in indirect heat exchange with a circulating heat exchange fluid. For example, the heat exchange fluid may be water or the methanol reactant passed to the first catalyst conversion stage. The second stage catalytic conversion operation is particularly restricted to converting the first stage effluent mixture comprising methanol, dimethyl ether and water to an olefin rich product material. The operation is highly exothermic and occurs rapidly in the presence of selected crystalline zeolites and particularly a catalyst comprising a ZSM-5 or related crystalline zeolite or a small pore crystalline zeolite.

In general, the zeolite catalysts used in accordance with this invention are crystalline zeolites having a silica/alumina ratio greater than 12 and a constraint index (CI) between about 1 and about 12. These zeolites and their use as conversion catalysts for lower aliphatic alcohols are described in the U.S. patents referred to above, particularly U.S. Pat. Nos. 3,894,106; 4,025,571; 4,058,576 and 4,148,835. The entire contents of these patents are incorporated herein by reference.

The preferred class of zeolites described above are exemplified by ZSM-5, ZSM-11, ZSM-12, ZSM-35, ZSM-38 and ZSM-48 with ZSM-5 being particularly preferred.

ZSM-5 is more particularly described in U.S. Pat. No. 3,702,886, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

ZSM-48 is more particularly described in U.S. Pat. No. 4,397,827, the entire contents of which are incorporated herein by reference.

Particularly preferred catalysts within the above description are zeolite catalysts made with large crystals, i.e. a crystal size of at least 1 micron, as described in U.S. Pat. Nos. 4,025,571 and 4,148,835, the entire contents of which are incorporated herein by reference. Another class of particularly preferred catalysts is the above-mentioned preferred catalysts which contain additional ingredients to improve ethylene selectively, such as amorphous silica interdispersed within the interior of the zeolite crystalline structure. Catalysts of this latter type are disclosed in U.S. Pat. Nos. 4,060,568 and 4,100,219, the entire contents of which are incorporated herein by reference.

In addition to ZSM-5 and related zeolites, other zeolites known in the art as small pore crystalline aluminosilicate zeolites may be employed in accordance with the present invention. These small pore zeolites may be either naturally occurring or synthetic and include, by way of example, erionite, chabazite, Zeolite T, Zeolite ZK-5 and ZSM-34. Zeolite T is described in U.S. Pat. No. 2,950,952, Zeolite ZK-5 in U.S. Pat. No. 3,427,195, and ZSM-34 in U.S. Pat. Nos. 4,079,095 and 4,079,096, the entire contents of all patents are incorporated herein by reference. The crystal structure of this class of zeolites suitable for use as catalysts in the process of this invention is such as to provide access to and egress from the intracrystalline free space of the zeolites by virtue of having pores, the major dimension of which is greater than 3 but less than 6 Angstrom units. These zeolites utilized herein are further characterized by pore windows of about a size such as would be provided by 8-membered rings of oxygen atoms. It will be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra.

The pores characterizing these zeolites useful in the present process may be substantially circular, such as in Zeolite ZK-5 having uniform pores of about 3.9 Angstroms or somewhat elliptical, such as in erionite having pores of approximately 3.6 by 5.2 Angstroms. It will be understood that, in any case, the small pore zeolites used as catalysts in the process of this invention have a major pore dimension of less than 6 Angstroms. The pore size dimensions of the above zeolites, as well as other feasible zeolites, are those specified in "Zeolite Frameworks" by W. M. Meier and D. H. Olson appearing in Advances in Chemistry Series, Vol. 101, pp. 155–170 (1971), the contents of which are incorporated herein by reference.

In the process employed with this invention, the conversion of the ether-rich effluent from the first dehydration stage to a highly olefinic hydrocarbon product is accomplished sequentially in a multi-stage adiabatic reactor system with interstage cooling. The cooling can be accomplished by either direct or indirect means. The zeolite conversion catalyst is provided in each of the stages as a fixed bed of catalyst. The quantity of catalyst in each bed is such that a uniform temperature rise occurs across each bed as the exothermic heat is released therein during the catalytic conversion of the feed to the highly olefinic product. The temperature rise across each bed and the quantity of catalyst in each bed is based on the desired overall conversion of the feed, the total adiabatic temperature increase for the methanol to olefin conversion and the sensitivity parameter for said conversion. By providing the catalyst in a sequential series of beds and providing interstage cooling to remove the exothermic heat of reaction, stable operation is obtained and undesirable conversion to gasoline boiling range hydrocarbons is substantially avoided.

The sensitivity parameter for a given chemical reaction and a given catalyst is a constant and can be approximated by assuming Arrhenius dependence of reaction rate on temperature and that the reaction rate is approximately linear over the temperature range of interest. Therefore, the sensitivity parameter can be calculated from the equation, $$\theta = \frac{R\, T_o^2}{E}$$

where
$\theta$ = sensitivity parameter
R = gas constant
To = initial temperature
E = activation energy For the conversion of methanol to ethylene, $\theta$ is equal to about 32.5° F.

When an exothermic chemical reaction is conducted in an adiabatic reactor, the conversion may be obtained from the equation:

$$X_A = \frac{\Delta T\, Cp}{(-\Delta H)}$$

where
$X_A$ = conversion
$\Delta T$ = adiabatic temperature rise
$\Delta H$ = heat of reaction
Cp = specific heat of feedstream in units of specific heat of the feedstream per mole of entering reactant Solving for $\Delta T$:

$$\Delta T = \frac{X_A\, (-\Delta H)}{Cp}$$

Therefore, the total adiabatic temperature rise for an exothermic chemical reaction at a specific conversion level and a given feed composition can be calculated from the specific heat of the feed and the heat of reaction.

For an exothermic reaction to be controllable and not overly sensitive to perturbation in flow rate, catalyst state, feed composition or inlet temperature when conducted in an adiabatic fixed bed of catalyst, the temperature rise in the bed must be limited to the sensitivity parameter, $\theta$. Where the total adiabatic temperature rise for the reaction is greater than the sensitivity parameter, multiple fixed beds must be employed to obtain the desired reaction under controllable conditions. The minimum number of beds required is equal to ($\Delta T$ total)/$\theta$. Where the ratio of the total adiabatic temperature rise to the sensitivity parameters is not a whole number the next higher whole number should be taken as the minimum number of fixed beds required.

Figure 1:
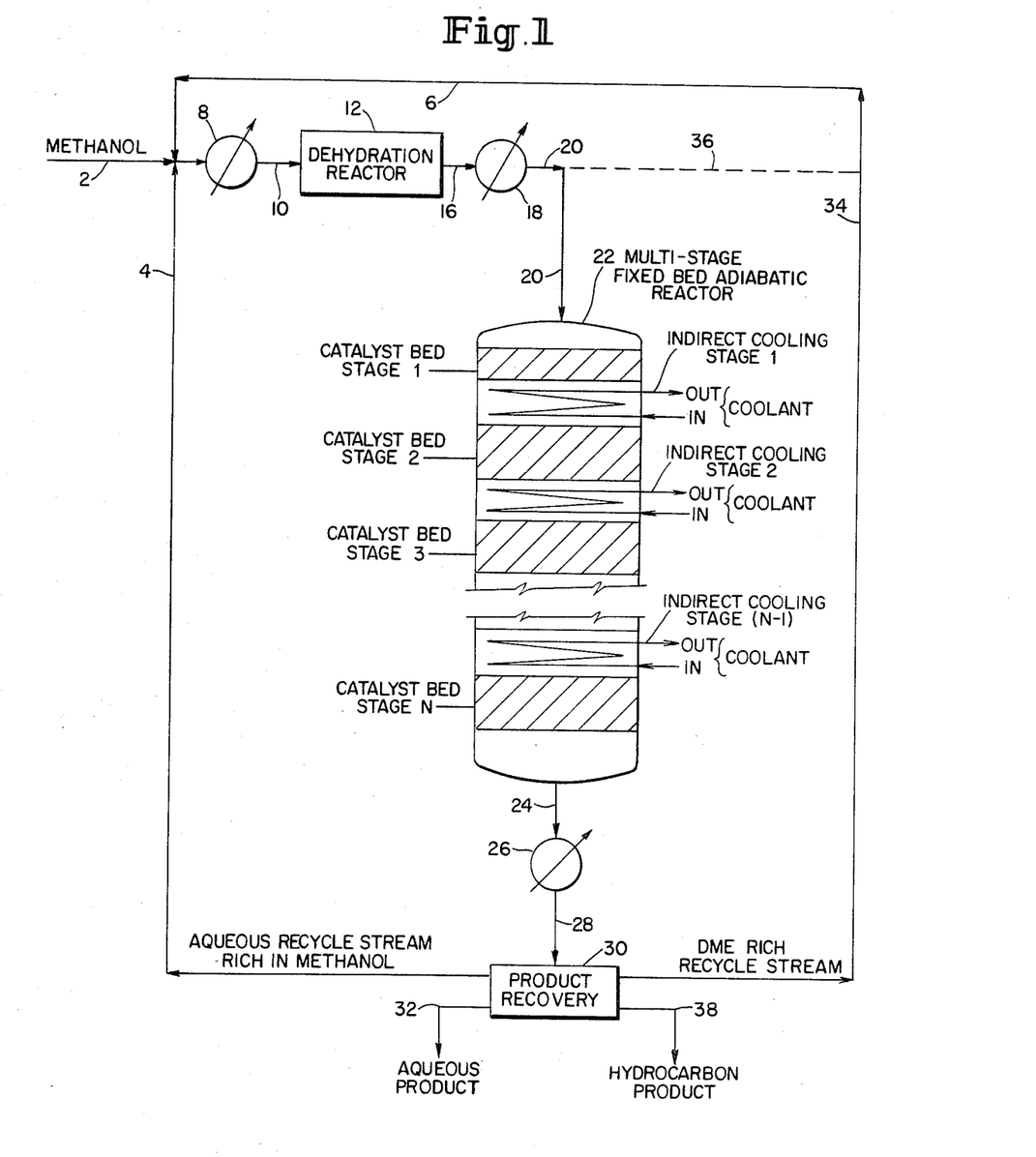
FIG. 1 is a schematic flow plan of an adiabatic multi-stage fixed bed reactor system for the conversion of methanol to olefinic hydrocarbons.

A schematic diagram of the process employed in this invention for partial conversion of methanol to a hydrocarbon product rich in light olefins and which process utilize a dehydration reactor in series with a multi-stage, fixed bed adiabatic reactor which includes interstage cooling by indirect means is shown in FIG. 1. Methanol feed containing nominally zero weight percent water up to about 80 weight percent water enters the process through line 2. It is mixed with an aqueous recycle stream which is rich in unreacted methanol from line 4 and a dimethyl ether (DME) rich recycle stream containing unreacted DME from line 6. The mixed stream is heated to reaction temperature (550°–700° F.) in heat exchanger 8 and passed through line 10 into dehydration reactor 12 where it is converted into an essentially equilibrium mixture of methanol, DME, and water. The equilibrium mixture leaves the dehydration reactor through line 16 and its temperature is adjusted within the range of 520°–700° F. in heat exchanger 18 prior to entering the multi-stage ZSM-5 fixed bed adiabatic reactor 22 via line 20.

The mixture then contacts the first-stage catalyst bed, hydrocarbons are formed and the temperature of the reactant/product mixture increases due to the exothermicity of the conversion process. The mixture leaving the first-stage catalyst bed is cooled by indirect heat exchange to a temperature equal to or substantially equal to that of the reactant mixture entering the first-stage catalyst bed. The cooled reactant/product mixture then enters the second-stage catalyst bed, additional conversion of reactants occurs liberating additional heat which raises the temperature of the reactant/product mixture. This mixture leaving the second-stage catalyst bed is cooled by indirect heat exchange to a temperature approximately that existing at the entrance to the first-stage catalyst bed. This conversion, heating, and cooling process continues in a manner similar to that described above until the last catalyst bed (stage) is reached, stage N. The mixture leaving the catalyst bed of stage (N−1) is cooled by indirect heat exchange and enters the catalyst bed of stage N. Upon exiting the stage N catalyst bed, the desired conversion level of methanol and DME has been achieved, and the heated product/reactant stream leaves the reactor through line 24, is cooled in heat exchanger 26 and passed via line 28 into product recovery section 30.

The cooled product/reactant mixture is present in three phases: (1) a liquid hydrocarbon phase, (2) an aqueous phase containing most of the unreacted methanol and some DME, and (3) a gaseous phase containing most of the light olefin hydrocarbon product and most of the unreacted DME.

The aqueous phase is subjected to several separation processes such as steam stripping, evaporation, and distillation to produce via line 4 an aqueous recycle stream which has a higher concentration of methanol than the raw aqueous phase produced by the conversion operation. This recycle stream also will contain most of the DME initially present in the aqueous phase. It may not be necessary to employ all of the separation processes mentioned to achieve the desired composition of the aqueous recycle stream. By the above treatment of the aqueous phase, most of the water produced by conversion of methanol to hydrocarbons and the water initially present in the feed methanol in line 2 is recovered and removed from the system by line 32 to yield an aqueous product containing only small quantities of methanol and DME (<0.5 wt %).

The gaseous phase remaining after condensation is compressed and sent to an absorber to recover unreacted DME. While they may differ in efficiency, suitable absorbents are methanol, methanol feed, and water. The DME-rich solution is then stripped to obtain a DME-rich stream suitable for recycling back to either the dehydration reactor through lines 34 and 6 or to the multi-stage fixed bed reactor through lines 34 and 36. The DME-lean stream from the absorber is then sent to an olefins recovery system similar to that employed in conventional olefin plants to recover ethylene, propylene, butenes, and a gasoline fraction through line 38.

As an alternative to the above, the gaseous phase may be compressed and sent to distillation type facilities to recover various hydrocarbons and DME for recycle as before.

The liquid hydrocarbon phase may be stabilized to recover light olefin products, and the stabilized liquid blended with gasoline range components recovered from the olefins recovery facility to make either finished gasoline or a gasoline blending stock.

The embodiment of FIG. 1 shows two different means of handling the DME recycle stream. The scheme used where all the unreacted DME is fed to the inlet of the dehydration reactor has been described. In some instances, it may be desirable to feed the unreacted DME in line 34 directly to the multi-stage fixed bed reactor by means of lines 36 and 20. The advantages of this latter operation are: (1) increased conversion of methanol to DME and water in the dehydration reactor, and (2) reduced heat load on the multi-stage reactor, since more of the feed enters as DME, which does not release as much heat when it is converted to hydrocarbons as does methanol. This reduced heat load increases the stability of the multi-stage reactor.

Figure 2:
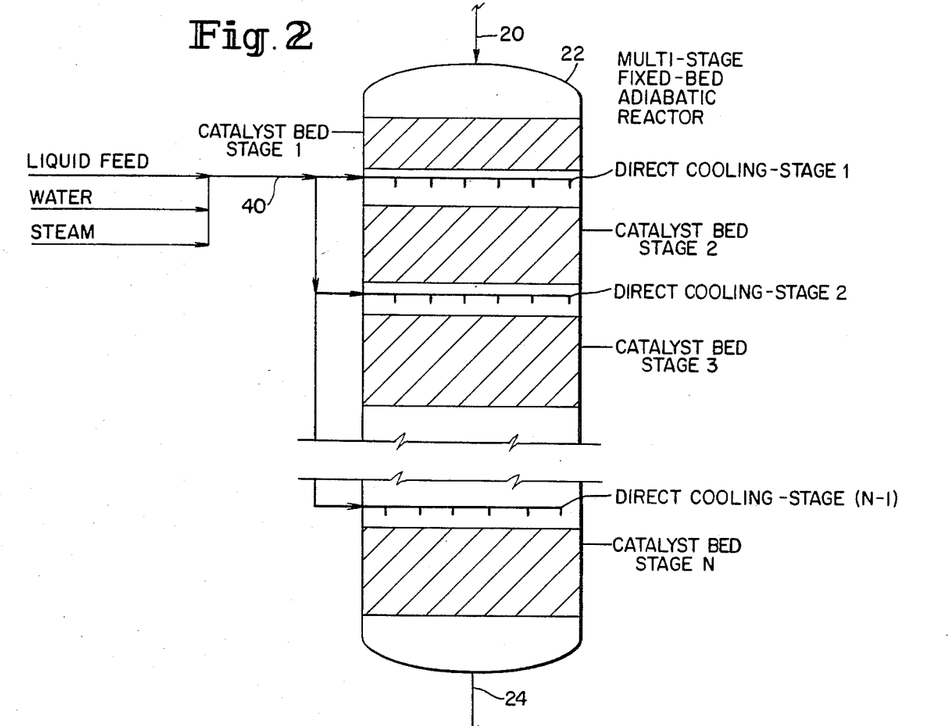
FIG. 2 is a schematic flow plan of a portion of FIG. 1 showing alternate means of interstage cooling.

Instead of indirect interstage cooling, it is possible to achieve the desired cooling in between the stages by direct quenching with (1) liquid feed, (2) water, or (3) low pressure steam (e.g., process steam at 50 psig). These optional embodiments are shown in FIG. 2 which depicts only that portion of FIG. 1 which would be modified to provide the direct cooling of these embodiments. Like numerals are employed in FIG. 2 to designate like equipment depicted in FIG. 1. In FIG. 2, the direct cooling fluids, obtained from a variety of sources, flow through line 40 and are directed to each of the interstage direct cooling means. A number of liquids obtained from the feed to the process may be employed for the quench cooling. The feed to dehydrator reactor 12, i.e., the combined streams from lines 2, 4 and 6, may be utilized. The other possible sources of liquid feed for direct cooling are the methanol feed from line 2, the aqueous phase recycle from line 4, the DME recycle from lines 6 or 34 or the condensate product from the dehydration reactor (a cooled stream from line 16). Other sources of direct cooling are water and low pressure (50 psig) process steam. The principal difference between the interstage direct cooling with water or steam and one of the process streams is that the process streams contain reactants which will be converted to olefins in the stages downstream of the direct cooling stage to which they are injected.

The following preferred operating conditions for a multi-stage adiabatic reactor are based on data obtained in a small-scale reactor. It is well known that high operating pressures result in reduced yields of light olefins. Therefore, the inlet pressure to the multi-stage reactor should be less than 100 psig, preferably less than 40 psig. It is not essential to house all stages in one vessel although this may be preferred for economic reasons. The interstage quenching involves a liquid injection system and a diffuser in the mixing zone in between the stages. The diameter of the fixed catalyst bed of each stage is usually between 5 and 20 feet (preferably between 8 and 15 feet). Pressure drop and economic considerations indicate that the space velocity (WHSV, based on total feed) should be in the range of 0.1–5. The preferable operating temperature range is about 520° to about 700° F. for zeolites having a constraint index of about 1–12 such as ZSM-5 and about 600° to about 900° F. for a small pore zeolite. Compensation for catalyst aging may be made by raising the inlet temperature to each stage. It is preferred to use a catalyst made with large crystal (at least about 1 micron) ZSM-5 zeolite in the multi-bed reactor, such as that disclosed in U.S. Pat. Nos. 4,025,571 and 4,148,835. The ZSM-5 catalyst may be unsteamed or presteamed to reduce its hexane cracking activity (alpha value). Under the operating conditions described here the alpha value should exceed 20. The catalyst may also contain additional ingredients which improve ethylene selectivity, such as, e.g., intracrystalline silica as described in U.S. Pat. Nos. 4,060,568 and 4,100,219. Of course, other suitable catalysts may also be employed.

It is preferred to limit the overall conversion level to hydrocarbons of methanol and DME to between about 10 and about 90%. At higher conversion levels, significant quantities of the methanol will be converted to aromatic compounds even at temperatures within the preferred range. To ensure partial conversion, it is essential that the reactor configuration and operating conditions do not result in an unstable or sensitive reactor operation (i.e., small perturbations in the operating conditions lead to excessive temperature rise and hence excessive conversion of desirable light olefins to gasoline boiling-range components). The methanol conversion reaction at partial conversion can be advantageously carried out in a multi-stage adiabatic reactor with interstage cooling. It is critical though to restrict the amount of heat generated in an individual reaction zone to prevent excessive conversion of desired light olefin products.

In accordance with the present invention, the stability of an adiabatic multi-stage fixed bed reactor is achieved by cofeeding small amounts of light olefins with the methanol feed entering the first-stage conversion reactor.

The conversion of methanol to olefinic and gasoline boiling hydrocarbons can be represented by a nonlinear autocatalytic kinetic model which can be described as follows:

$$A \rightarrow B \rightarrow C \qquad (1)$$

$$A + B \rightarrow 2B \qquad (2)$$

wherein A is the $CH_2$ in oxygenates; B represents light olefins ($C_2$, $C_3$, $C_4$) and C represents other hydrocarbons (paraffins+aromatics+naphthenes+heavy olefins).

The reaction scheme set forth by reactions 1 and 2 above clearly show an initial induction period for methanol/DME conversion, and then a rapid increase in the reaction rate as small amount of light olefins (B) are formed.

Figure 3:
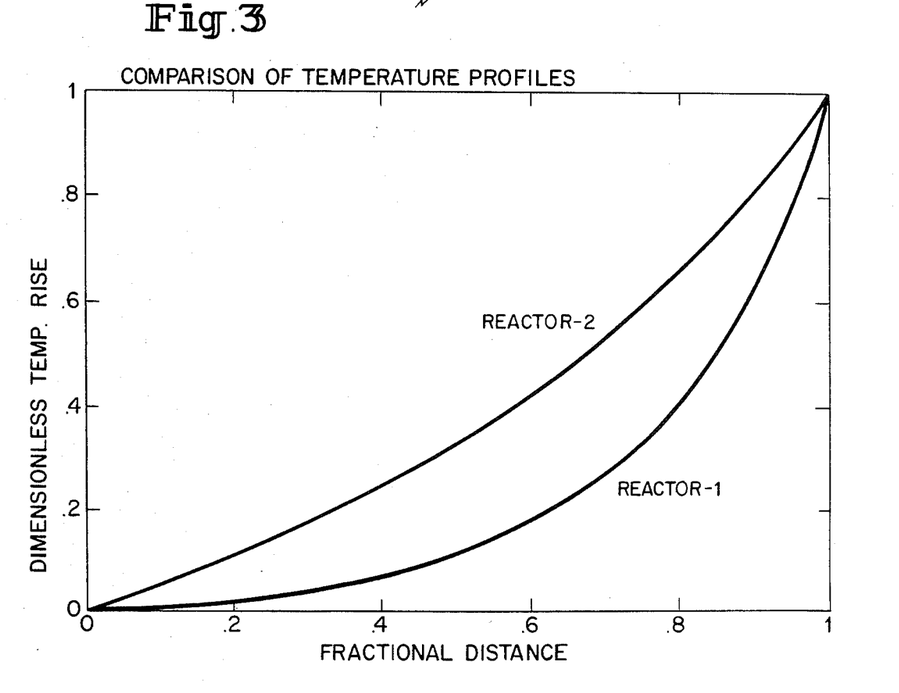
FIG. 3 is a graph comparing temperature profiles across the first and second stages of the adiabatic reactor employed in the present invention.

Using the above kinetic model, the behavior of a multi-stage adiabatic reactor system has been simulated. The simulation studies indicate that the first-stage is more sensitive to perturbations in the operating conditions and the sensitivity is reduced when small quantities of light olefins (B) are added to the feed containing oxygenates of methanol and/or DME (A). The following examples when taken in consideration with FIGS. 3, 4, and 5 best illustrate the present invention.

EXAMPLE 1

This example illustrates the simulation of a multi-stage adiabatic reactor in which each stage was run at WHSV=12 $hr^{-1}$ using a test catalyst of HZSM-5C which has been presteamed. Table 1 summarizes the results for a ten-stage adiabatic reactor designed to achieve about 87% overall conversion. Each stage had equal amounts of catalyst, and temperature rise per stage was desired to be between 16.0° and 17.5° C. This Example can be considered a base case.

TABLE 1

| | 10-Stage Adiabatic Reactor Using The Test Catalyst | | |
|---|---|---|---|
| Stage No. | Inlet Temperature (°K.) | Overall Conversion % | Temperature Rise per Stage (°K.) |
| 1 | 649 | 9.0 | 17.1 |
| 2 | 607 | 18.7 | 16.6 |
| 3 | 594 | 28.2 | 16.2 |
| 4 | 588 | 37.8 | 16.3 |
| 5 | 585 | 47.2 | 16.6 |
| 6 | 584 | 56.5 | 16.9 |
| 7 | 584 | 65.2 | 16.6 |
| 8 | 586 | 73.5 | 17.1 |
| 9 | 589 | 80.9 | 17.3 |
| 10 | 593 | 87.0 | 17.4 |

One important observation is the difference in the inlet temperatures of the first two stages.

EXAMPLE 2

To study the sensitivity of each stage to temperature perturbations, the behavior of the first three stages in the previous Example were simulated. A ±3° C. perturbation to the first stage inlet temperature was considered, stages 2 and 3 were kept at the same temperature as indicated in Table 1. The results are presented in Table 2 and 3.

TABLE 2

| Temperature Rise in the First Stage Affects the Subsequent Stages | | |
|---|---|---|
| +3° C. perturbation to the inlet temperature of the first stage | | |
| Stage No. | Inlet Temperature °K. | Temperature Rise ΔT, °K. |
| 1 | 652 | 34.4 |
| 2 | 607 | 29.4 |
| 3 | 594 | 22.6 |

TABLE 3

| Temperature Rise in the first Stage Affects the Subsequent Stages | | |
|---|---|---|
| −3° C. perturbation to the inlet temperature of the first stage | | |
| Stage No. | Inlet Temperature °K. | Temperature Rise ΔT, °K. |
| 1 | 646 | 10.1 |
| 2 | 607 | 10.3 |
| 3 | 594 | 10.5 |

It can be concluded from Tables 2 and 3 that increasing the ΔT in the first stage results in increased ΔT in the subsequent stages, and the reverse is also true.

This phenomenon is related to the autocatalysis, the overall conversion of (A) being dependent on the concentration of (B). By changing the conversion in the first stage the concentration of (B) in the second stage is changed. In Table 2 the concentration of (B) is increased in the second stage above the base case concentration. This results in increased conversion and therefore the temperature rise in the second stage. This effect decreases as conversion proceeds in the downstream direction. Thus one would expect that in the last few stages conversion and temperature rise will decrease compared to the base case, due to excessive conversion in the previous stages.

EXAMPLE 3

The sensitivity of each stage to a +3° C. perturbation in the inlet temperature over the base case for the first three stages is summarized in Table 4. From the last column of Table 4 it can be seen that a +3° C. perturbation in the inlet temperature to each stage, maintaining the others at the base case conditions, results in 17.3°, 5.0° and 4.1° C. increase in the temperature rise above the base case temperature rise, respectively. Thus it is seen that the first stage is most sensitive and the sensitivity decreases in the downstream direction. Therefore, to maintain a stable reactor operation, it is advisable to take lower ΔT, i.e., conversion per stage, in the first few stages rather than designing a reactor to achieve constant conversion per stage.

TABLE 4

| Sensitivity of the Stages to Inlet Temperature Perturbations | | | |
|---|---|---|---|
| Stage No. | Inlet Temperature °K. | Temperature Rise in a Stage (ΔT) (°K.) | Increase in ΔT Over the Base Case ΔT (°K.) |
| a. +3° C. perturbation, first stage | | | |
| 1 | 652 | 34.4 | 17.3 |
| 2 | 607 | 29.4 | 12.8 |
| 3 | 594 | 22.6 | 6.4 |
| b. +3° C. perturbation, second stage | | | |

TABLE 4-continued

Sensitivity of the Stages to
Inlet Temperature Perturbations

| Stage No. | Inlet Temperature °K. | Temperature Rise in a Stage (ΔT) (°K.) | Increase in ΔT Over the Base Case ΔT (°K.) |
|---|---|---|---|
| 1 | 649 | 17.1 | — |
| 2 | 610 | 21.6 | 5.0 |
| 3 | 594 | 18.2 | 2.0 |
| c. +3° C. perturbation, third stage | | | |
| 1 | 649 | 17.1 | — |
| 2 | 607 | 16.6 | — |
| 3 | 597 | 20.3 | 4.1 |

From the above discussion, it is apparent that the concentration of light olefins (B) plays a crucial role in the behavior of the first few stages. The higher sensitivity of the first stage is related to the accelerating effect of reaction rate due to olefin formation. This is reflected in the temperature profiles of the reactors. To illustrate this point, the temperature profiles from the first two stages can be compared in FIG. 3. From FIG. 3 it is seen that the temperature profile of the first stage is much sharper towards the end of the bed compared to the temperature profile of the second stage, which is much more gradual. It can also be shown that increasing the catalyst fill in the first stage does not improve stability therein where again the temperature profile in the first stage is much sharper than the second stage.

Figure 4:
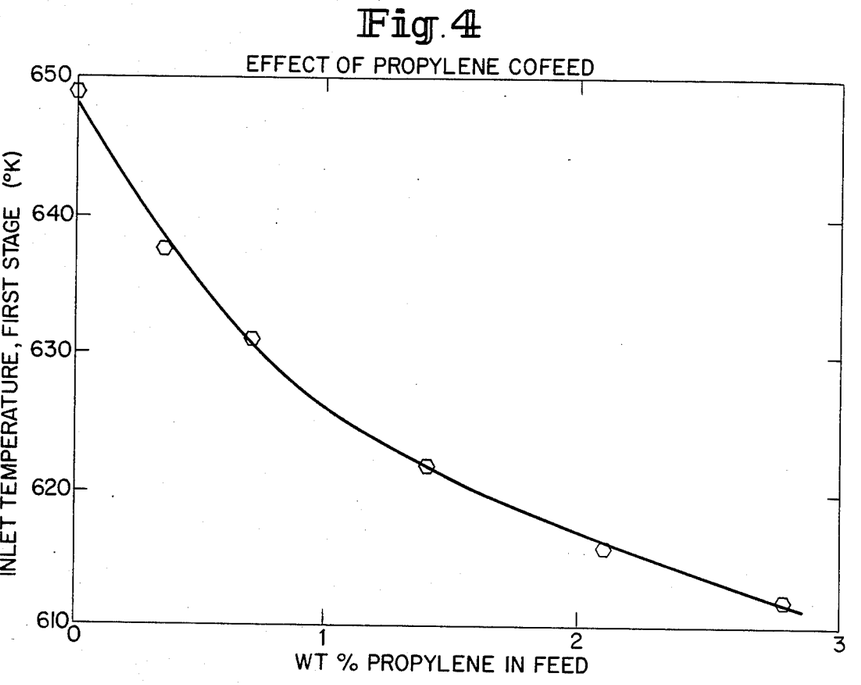
FIG. 4 is a graph illustrating the effect of cofed propylene on the inlet temperature of the first stage.

In accordance with the present invention, the sensitivity of the first stage is reduced by cofeeding light olefins with the methanol and/or dimethyl ether feed. The addition of light olefins to the feed necessitates decreasing the inlet temperature of the first and subsequent stages to maintain a constant ΔT of 16° to 17.5° C. per stage. FIG. 4 shows the effect of cofeeding propylene with 50/50 (W/W) MeOH/H₂O feed on the inlet temperature of the first stage for the base case. Inlet temperature of the second and subsequent stages is effected to a much lesser extent, see Table 5. Addition of 1 wt % propylene corresponds to a 25° C. decrease in the inlet temperature of the first stage. In Table 5 is represented a base case designed for a three stage rector with 0.7 wt % propylene in the feed.

TABLE 5

3-Stage Design with 0.7 wt % Propylene in the Feed

| Stage No. | Inlet Temperature (°K.) | Overall Conversion % | Temperature Rise per Stage (°K.) |
|---|---|---|---|
| 1 | 630 | 8.9 | 16.4 |
| 2 | 603 | 18.7 | 16.7 |
| 3 | 592 | 28.3 | 16.4 |

EXAMPLE 4

To show the improvement in the stability in the reactor due to olefin cofeeding, this example again illustrates the effect of a ±3° C. perturbation to inlet temperature of the first stage, other stages are maintained at conditions of Table 5. These results are summarized in Table 6. The improved stability is seen by comparing Tables 4a and 6a.

TABLE 6

Olefin Cofeeding Improves the Stability of the Reactor
0.7 wt % propylene in the feed

| Stage No. | Inlet Temperature °K. | Temperature Rise in a Stage (ΔT) (°K.) | Increase in ΔT Over the Base Case ΔT (°K.) |
|---|---|---|---|
| a. +3° C. perturbation to the inlet temperature of the first stage | | | |
| 1 | 633 | 23.5 | 7.3 |
| 2 | 603 | 22.6 | 5.9 |
| 3 | 592 | 20.4 | 4.1 |
| b. −3° C. perturbation to the inlet temperature of the first stage | | | |
| 1 | 627 | 11.9 | 4.3 |
| 2 | 603 | 13.0 | 3.7 |
| 3 | 592 | 13.2 | 3.1 |

Without olefin cofeed, a +3° C. perturbation resulted in 17.3° C. temperature rise over the base case whereas for 0.7 wt % addition of propylene, the temperature rise reduced to 7.3° C. over the base case. Thus, the reactor operation is less sensitive when olefins are cofed to the multi-sage adiabatic reactor. If we compare Tables 2 and 6, it is seen that ±3° C. perturbation in inlet temperature with olefin cofeed results in a deviation from the base design to a much lesser extent, i.e., reactor operation is much smoother.

Figure 5:
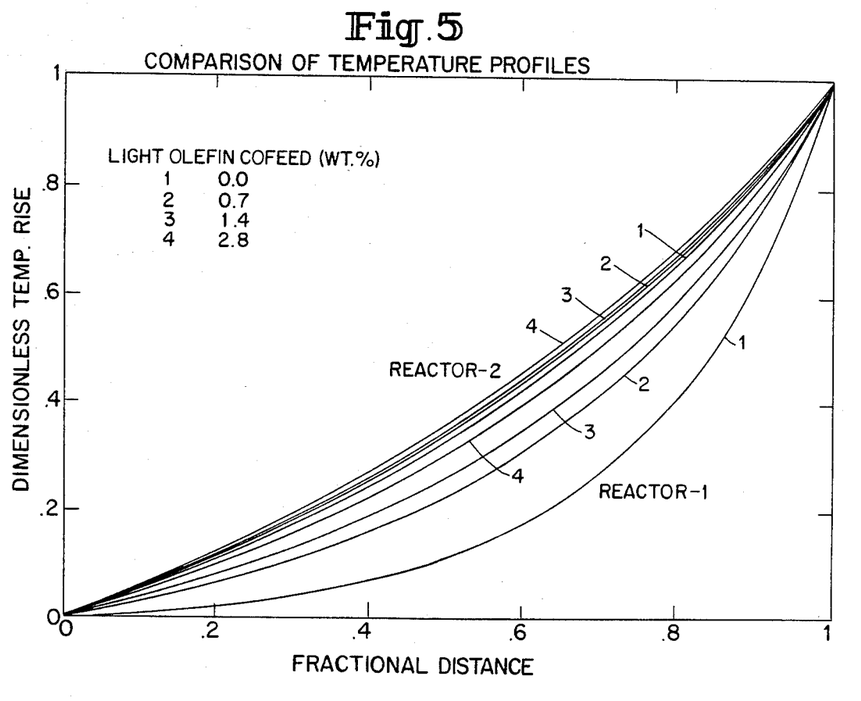
FIG. 5 is a graph illustrating the effect of varying amounts of cofed olefins on the temperature profile of the first and second stages of the reactor.

The improved stability of the reactor system with olefin cofeeding is schematically represented in FIG. 5. In FIG. 5, the shapes of temperature profiles of the first two adiabatic stages with varying amounts of light olefins in the feed (e.g., 0–2.8 wt.% propylene) is compared. It can be seen from FIG. 5 that with increased propylene addition to the feed, the temperature profiles of the two stages come closer to each other. Of course, this corresponds to improvement in the stability of the first stage with increased amounts of propylene in the feed. FIG. 5 clearly shows that 0.7 wt.% addition significantly reduces the sharpness of temperature profile of the first stage and each incremental addition of propylene has less impact on the improvement in the stability.

In the above examples, propylene was chosen as a cofeeding agent. It should be emphasized, however, that identical effects for ethylene, propylene, or butene addition would be obtained. It is known that the reactivity of these light olefins is different, e.g., propylene is much more reactive than ethylene, therefore, experimentally the impact of propylene addition will be more significant than ethylene addition. The optimum amount of cofed olefin needed to achieve improved stability and decrease inlet temperature will thus vary according to the olefin which is cofed and various reactor designs. An olefin addition of about 0.5 to 3 wt.% can represent a broad range which would be applicable in the present invention.

The olefin cofeeding agent can be produced in-situ during dehydration of the methanol feed to the ether-rich equilibrium product. Thus, alcohols such as ethanol, 1-propanol, isopropanol, butanol, etc. that dehydrate to the desired light olefins can be cofed with the methanol to the dehydration reactor.

EXAMPLE 5

An experimental study was performed in a laboratory multi-stage adiabatic reactor with four stages. The first stage was used as a dehydration reactor containing 35 g of gamma alumina dehydration catalyst. The remaining three stages contained 20 g each of presteamed HZSM-5C catalyst, wherein MeOH/DME were converted to hydrocarbon products. A small quantity of isopropanol liquid was added to the feed (50/50 (W/W) MeOH/water) going to the dehydration stage which provided an in-situ source of propylene. The isopropanol is converted to propylene on the dehydration catalyst. Thus, the stream entering the first conversion stage contained MeOH, DME, water and propylene. Experiments were also conducted without isopropanol added to the feed as a comparison.

It was found that the addition of 2-3 cc/hr of isopropanol to 265 cc/hr of feed improved the stability of the reactor system significantly. Table 7 summarizes the results with-and without the addition of isopropanol to the feed.

TABLE 7

Effect of Olefin Cofeeding on Reactor Performance

| Cofeed ~1% Isopropanol | No | Yes |
|---|---|---|
| Catalyst | HZSM-5C | HZSM-5C |
| Water Dilution | 1:1 | 1:1 |
| Days On-Stream | 31 | 33 |
| Inlet Temperature, °F. | | |
| Dehydration Reactor | 622 | 622 |
| Conversion Reactor 1 | 695 | 635 |
| Conversion Reactor 2 | 560 | 553 |
| Conversion Reactor 3 | 562 | 559 |
| Temperature Rise/Bed, °F. | | |
| Dehydration Reactor | 87 | 87 |
| Conversion Reactor 1 | 15 | 33 |
| Conversion Reactor 2 | 33 | 48 |
| Conversion Reactor 3 | 26 | 43 |
| Average Conversion, % | 24 | 33 |

In the experiment, the stability of the first conversion reactor stage is shown to be most important. Thus, increasing the allowable temperature rise in the first conversion stage results in increase temperature rise in the subsequent stages and thus the controllability of the first conversion stage is imperative for overall stability of the process. From Table 7 it is seen that without isopropanol addition, maximum achievable stable $\Delta T$ before reactor runaway in the first conversion stage was 10°-15° F. Addition of isopropanol resulted in a stable $\Delta T$ of about 30°-35° F. in the first conversion stage. Improvement in the performance of subsequent stages to some extent was also noticed. The overall conversion increased from 24 to 33 percent.

In addition to improved controllability of the reactor system the resultant lower inlet temperature requirement of the first stage with cofed isopropanol results in decreased catalyst aging rate.

EXAMPLE 6

Figure 6:
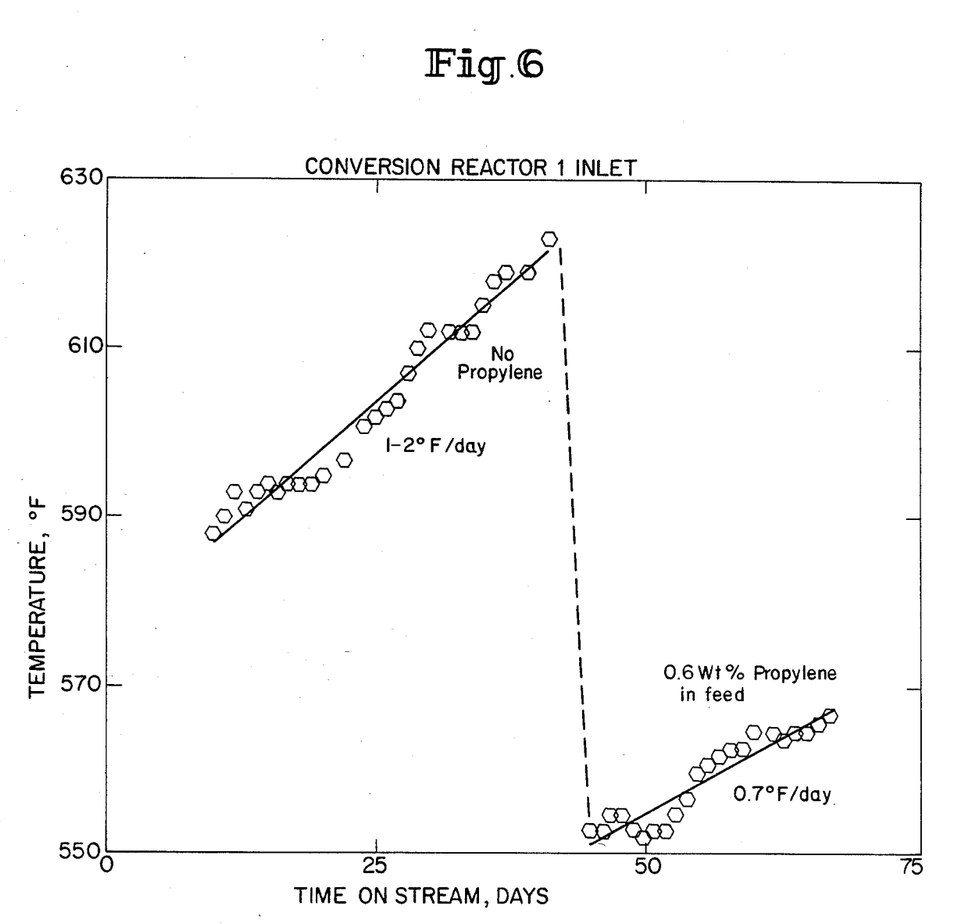
FIG. 6 is a graph illustrating the effect olefin addition has on the aging rate of a conversion catalyst in the first conversion reactor.

An experimental study was performed in a laboratory multi-stage adiabatic reactor system mentioned in the previous example to demonstrate the effect of propylene addition on the aging rate of the first conversion reactor. The feed was 50/50 (W/W) MeOH/water going to the dehydration stage. After about 40 days on stream (0.6 wt.% propylene was added to the feed. The resultant inlet temperatures of the first conversion stage as a function of time on stream are plotted in FIG. 6. From FIG. 6, it is seen that 0.6 wt.% addition of propylene resulted in 65° F. decrease in the inlet temperature requirement. Also, the aging rate is decreased from 1.2° F./day before propylene addition to 0.7° F./day after propylene addition. The average temperature rise across the first stage was 20° F. before the propylene addition and 30° F. after the propylene addition, confirming the improved reactor stability results of the previous example. Thus, it is shown that light olefin cofeeding reduces the catalyst aging rate of the first conversion reactor even when the average conversion across the first stage is higher.

What is claimed is:

1. In a process for converting lower aliphatic alcohols into a predominantly olefinic hydrocarbon product by (a) contacting a feed comprising said aliphatic alcohol with a dehydration catalyst at elevated temperatures and exothermic reaction conditions effective to convert said alcohol to an ether-rich product, and (b) contacting the ether-rich product with at least a plurality of fixed beds of crystalline aluminosilicate zeolite in a sequential manner at elevated temperatures at substantially the same temperature increases across each of said fixed beds and under exothermic reaction conditions effective to convert said ether-rich product, at a predetermined conversion, to olefinic hydrocarbons, and cooling the reaction mixture effluent from each of said fixed beds, except the last, to reduce the temperature of said effluent by an amount substantially equal to the temperature increase across each fixed bed, the improvement comprising cofeeding with said ether-rich product about 0.5-3 percent by weight of a light olefin to the first of said fixed beds to stabilize the operation of said fixed beds whereby the shapes of the temperature profiles of the individual fixed beds are closer to each other allowing increased stable temperature rise in each stage.

2. The improvement of claim 1 wherein said cofed light olefin comprises $C_2$-$C_4$ olefins.

3. The improvement of claim 1 wherein said cofed olefin is propylene.

4. The improvement of claim 3 wherein the amount of cofed olefin is no greater than 1.5 weight percent of said ether-rich product.

5. The improvement of claim 4 wherein the amount of cofed olefin is about 0.7 percent by weight.

6. The improvement of claim 1 wherein said cofed light olefin is formed by cofeeding the corresponding alcohol of said light olefin with said aliphatic alcohol feed for contact over said dehydration catalyst.

7. The improvement of claim 6 wherein said cofed olefin is propylene, said propylene being produced by cofeeding isopropanol for contact with said dehydration catalyst.

8. The improvement of claim 1 wherein said crystalline aluminosilicate zeolite present in said fixed beds is ZSM-5 zeolite.

9. The improvement of claim 8 wherein the ZSM-5 zeolite has a crystal size of at least about 1 micron.

10. The improvement of claim 8 wherein amorphous silica is interdisposed within the interior of said crystalline structure of said zeolite.

11. The improvement of claim 1 wherein said crystalline aluminosilicate zeolite present in said fixed beds is erionite or ZSM-34.

12. The improvement of claim 1 wherein the dehydration catalyst is gamma alumina.

13. The imrovement of claim 1 wherein the exothermic reaction conditions in said fixed beds include a pressure of less than 100 psig and a space velocity of 0.1-5 WHSV.

14. The improvement of claim 1 wherein said lower aliphatic alcohol is methanol and wherein the feed for contacting with said dehydration catalyst is a methanol-water feed containing about 0 to about 70 wt.% water or an equivalent methanol-water feed.

15. The improvement of claim 1 wherein the predetermined conversion is between about 10 and about 90 percent.

16. The improvement of claim 1 wherein the temperature rise across each of the plurality of fixed beds is between about 18° and 45° F.

17. The improvement of claim 1 wherein the minimum number of fixed beds is from 2 to 10.

18. The improvement of claim 8 wherein the elevated temperatures in said fixed beds are in the range of from about 520° to about 750° F.

19. The improvement of claim 11 wherein the elevated temperatures in said fixed beds are in the range of about 600° to 900° F.

* * * * *